United States Patent
Merkel et al.

(10) Patent No.: US 9,211,483 B2
(45) Date of Patent: *Dec. 15, 2015

(54) LOW TEMPERATURE PRODUCTION OF 2-CHLORO-3,3,3-TRIFLUOROPROPENE

(71) Applicant: Honeywell International Inc., Morristown, NJ (US)

(72) Inventors: Daniel C. Merkel, West Seneca, NY (US); Hsueh Sung Tung, Getzville, NY (US); Konstantin A. Pokrovski, Orchard Park, NY (US); Haiyou Wang, Amherst, NY (US); Selma Bektesevic, Williamsville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 92 days.

This patent is subject to a terminal disclaimer.

(21) Appl. No.: 14/168,475

(22) Filed: Jan. 30, 2014

(65) Prior Publication Data

US 2014/0147343 A1    May 29, 2014

Related U.S. Application Data

(62) Division of application No. 13/313,085, filed on Dec. 7, 2011, now Pat. No. 8,680,345.

(60) Provisional application No. 61/430,630, filed on Jan. 7, 2011.

(51) Int. Cl.
  *B01D 3/00*  (2006.01)
  *C07C 17/20*  (2006.01)
  *C07C 17/25*  (2006.01)
  *C07C 17/383*  (2006.01)

(52) U.S. Cl.
  CPC .............. *B01D 3/009* (2013.01); *C07C 17/206* (2013.01); *C07C 17/25* (2013.01); *C07C 17/383* (2013.01)

(58) Field of Classification Search
  CPC ........................................................ B01D 3/00
  USPC ......................................................... 422/187
  See application file for complete search history.

(56) References Cited

U.S. PATENT DOCUMENTS

| | | | |
|---|---|---|---|
| 5,767,322 A * | 6/1998 | Zakoshansky et al. | 568/571 |
| 6,844,475 B1 * | 1/2005 | Tung et al. | 570/168 |
| 7,795,480 B2 | 9/2010 | Merkel et al. | |
| 2005/0033097 A1 | 2/2005 | Tung et al. | |

(Continued)

FOREIGN PATENT DOCUMENTS

WO    2010123148 A1    10/2010

OTHER PUBLICATIONS

International Search Report, mailing date of Jul. 30, 2012, issued in corresponding International Application No. PCT/US2012/020302.

*Primary Examiner* — Walter D Griffin
*Assistant Examiner* — Huy-Tram Nguyen
(74) *Attorney, Agent, or Firm* — Bruce O. Bradford

(57) ABSTRACT

Disclosed is a method for the production of 1233xf comprising the continuous low temperature liquid phase reaction of 1,1,1,2,3-pentachloropropane and anhydrous HF, without the use of a catalyst, wherein the reaction takes place in one or more reaction vessels, each one in succession converting a portion of the original reactants fed to the lead reaction vessel and wherein the reactions are run in a continuous fashion.

3 Claims, 2 Drawing Sheets

(56) References Cited

U.S. PATENT DOCUMENTS

| | | |
|---|---|---|
| 2009/0030244 A1 | 1/2009 | Merkel et al. |
| 2009/0062576 A1 | 3/2009 | Eicher et al. |
| 2009/0240090 A1* | 9/2009 | Merkel et al. ............ 570/160 |
| 2010/0185030 A1 | 7/2010 | Elsheikh et al. |
| 2011/0004035 A1 | 1/2011 | Merkel et al. |
| 2011/0160499 A1 | 6/2011 | Wendinger et al. |
| 2011/0245548 A1 | 10/2011 | Merkel et al. |

* cited by examiner

LOW TEMPERATURE PRODUCTION OF 2-CHLORO-3,3,3-TRIFLUOROPROPENE

CROSS-REFERENCE TO RELATED APPLICATION

This application is a divisional of commonly owned, copending application Ser. No. 13/313,085 filed Dec. 7, 2011, now U.S. Pat. No. 8,680,345. Application Ser. No. 13/313,085 claims domestic priority from commonly owned, U.S. Provisional Patent Application Ser. No. 61/430,630, filed Jan. 7, 2011. The disclosures of these applications are incorporated herein by reference.

FIELD OF THE INVENTION

This invention relates to methods and systems for producing hydrochloro-fluoroolefins, particularly 2-chloro-3,3,3-trifluoropropene (also known as HCFO-1233xf, or 1233xf) which is useful as intermediate in the production of 2,3,3,3-tetrafluoropropene (also known as HFO-1234yf or 1234yf). 1233xf can also be used as a monomer in production of chlorofluoropolymers.

BACKGROUND OF THE INVENTION

Processes for synthesizing 1233xf are known. For example, U.S. Pat. No. 7,795,480 discloses a process for preparing 1233xf via the gas-phase reaction of 1,1,2,3-tetrachloropropene, 2,3,3,3-tetrachloropropene, or 1,1,1,2,3-pentachloro-propane with hydrogen fluoride (HF) in the presence of a catalyst and a stabilizer. However, this process suffers from catalyst deactivation resulting in a low yields and a need for catalyst regeneration.

Other processes for the production of 1233xf exist. See for example, U.S. Patent Application Ser. No. 61/202,966, which discloses a method of 1233xf production via vapor phase non-catalytic fluorination of tetrachloropropene or pentachloropropane at high temperatures exceeding 300° C. This method suffers from low yields due to instability of starting materials at high temperature in the presence of HF which facilitates undesired side reactions resulting in undesired by-product formation.

The high operating temperatures and undesired by-product formation disclosed in the above referenced documents result in high operating and production costs. Accordingly, there remains a need for a process for producing 1233xf in high yields. This invention satisfies that need.

SUMMARY OF THE INVENTION

The current invention solves these problems by producing 1233xf via the continuous low temperature liquid phase reaction of 1,1,1,2,3-pentachloropropane (also known as HCC-240db or 240db) with anhydrous HF, without use of a catalyst. However, without the use of a catalyst, the problem of slower reaction rates is introduced. The present inventors have solved this problem by the use of a series of reaction vessels, each one in succession converting a portion of the original reactants fed to the lead reactor and run in a continuous fashion. The number of reactors in a particular train is determined by their size (bigger means more capital money is required, but fewer would be required) and the desired production rate of 1233xf. At least one reactor can be used. Preferably, at least two reactors can be used. More preferably, at least three reactors can be used. Most preferably, more than three reactors can be used.

As an example, the lead reactor converts 70% of the 240db feed, of which only 50% is converted to the desired product, while the rest is only partially fluorinated to produce intermediates including compounds such as 1,1,2,3-tetrachloro-1-fluoropropane (HCFC-241db or 241db), 1,2,3-trichloro-1,1-difluoropropane (HCFC-242db or 242db), and 2,3-dichloro-1,1,1-trifluoro-propane (HCFC-243db or 243db), 2,3,3-trichloro-3-fluoropropene (HCFO-1231xf), 2,3-dichloro-3,3-difluoropropene (HCFO-1232xf) among others. The unconverted 240db and under-fluorinated intermediates are high boiling compounds relative to 1233xf and will not exit the attached stripping column.

A continuous stream of unconverted 240db, under-fluorinated intermediates, and some unreacted HF are taken from the bottom of the reactor and fed to a second reactor. Here more of the original reactants and intermediates are converted to 1233xf which exits the top of the attached stripping column. Fresh HF may need to be added. As before a continuous stream of unconverted 240db, under-fluorinated intermediates, and some unreacted HF are taken from the bottom of the second reactor and fed to a third reactor where more is converted. Again fresh HF may need to be added. This reactor train continues in series until the desired production rate of 1233xf is achieved.

Accordingly, an aspect of the invention provides a method for producing a 1233xf comprising:

(a) providing a liquid reaction admixture comprising hydrogen fluoride and 1,1,1,2,3-pentachloropropane, wherein said hydrogen fluoride and 1,1,1,2,3-pentachloropropane are present in a molar ratio of greater than about 3:1 and (b) reacting said hydrogen fluoride and 1,1,1,2,3-pentachloropropane in a liquid phase and at a reaction temperature of from about 65° C. to about 175° C. using one or more, preferably two or more, stirred reactors in series to produce reaction product streams comprising 2-chloro-3,3,3-trifluoropropene, hydrogen chloride, unreacted hydrogen fluoride, and optionally unreacted 1,1,1,2,3-pentachloropropane.

Preferably, the method further comprises the steps;

(c) contacting said combined reaction product streams with a heat exchanger to produce:

(i) a first crude product stream comprising a majority of said hydrogen chloride, a majority of said 2-chloro-3,3,3-trifluoropropene, and at least a portion of said unreacted hydrogen fluoride, wherein said portion is an amount sufficient to form an azeotrope with one or more of said 2-chloro-3,3,3-trifluoropropene, and (ii) a reflux component comprising a majority of said unreacted hydrogen fluoride and under-fluorinated intermediates; and (d) returning said reflux component to said reaction admixture.

In certain preferred embodiments, the method further comprises one or more of the following steps:

(e) separating unreacted reactants, including unreacted 1,1,1,2,3-pentachloropropane and/or under-fluorinated intermediates (e.g., 1,1,2,3-tetrachloro-1-fluoropropane, 1,2,3-trichloro-1,1-difluoropropane, 2,3-dichloro-1,1,1-trifluoropropane, 2,3,3-trichloro-3-fluoropropene (HCFO-1231xf), 2,3-dichloro-3,3-difluoropropene (HCFO-1232xf)) via distillation and recycling these unreacted reactants and under-fluorinated intermediates back to the reactor;

(f) removing at least a portion, and preferably a majority, of hydrochloric acid by-product;

(g) separating and recycling unreacted HF in a crude product stream via a sulfuric acid adsorption or a phase separation; and (h) distillation of the crude product stream to separate 1233xf from reaction by-products.

According to another aspect of the invention, provided herein is an integrated system for producing 1233xf comprising:

(a) one or more feed streams cumulatively comprising hydrogen fluoride and 1,1,1,2,3-pentachloropropane;

(b) a liquid phase reactor system consisting of a series (train) of two or more agitated reactors each fed by its predecessor, each combined with attached stripping column (supplied with low-temperature cooling), maintained at a first temperature of from about 65° C. to about 175° C., wherein said liquid phase reactor series is fluidly connected to said one or more feed streams;

(c) a stripping system comprising a stripping column, a reflux stream fluidly connected to said stripping column, and a combined first crude product stream fluidly connected to said stripping column, wherein said reflux stream is fluidly connected to said lead liquid phase reactor;

(d) a hydrogen chloride removal system comprising a first distillation column, a hydrogen chloride by-product stream fluidly connected to said first distillation column, and a second crude product stream fluidly connected to said first distillation column, wherein said first distillation column is fluidly connected to said stripping column;

(e) a hydrogen fluoride recovery system comprising a sulfuric acid absorption and recycle system or a phase separation vessel, a second recycle stream comprising hydrogen fluoride fluidly connected to said sulfuric acid absorption and recycle system or a phase separation vessel, a third product stream comprising 2-chloro-3,3,3-trifluoropropene fluidly connected to said sulfuric acid absorption and recycle system or a phase separation vessel, wherein said sulfuric acid absorption and recycle system or a phase separation vessel is fluidly connected to said second crude product stream; and (f) a 2-chloro-3,3,3-trifluoropropene purification system comprising a second distillation column fluidly connected to said third product stream; a final product stream comprising 2-chloro-3,3,3-trifluoropropene fluidly connected to said second distillation column; a second by-product stream fluidly connected to said distillation column.

DETAILED DESCRIPTION OF THE INVENTION

In preferred embodiments, the invention involves a fully integrated manufacturing process for making 2-chloro-3,3,3-trifluoropropene (1233xf) as described below.

The reaction chemistry for this process involves a single-step reaction of 1,1,1,2,3-pentachloropropane with anhydrous HF in a liquid-phase, uncatalyzed reactor to produce primarily 2-chloro-3,3,3-trifluoropropene (1233xf) plus HCl as a by-product.

Preferably, the reaction is maintained under conditions (temperature, pressure, residence time) to increase yield of 1233xf. Accordingly, the desired reactions involve:

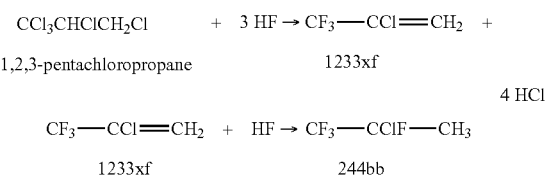

Undesired reactions, which are preferably avoided, include:

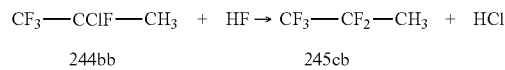

In certain embodiments, the manufacturing process comprises five major unit operations:

(1) fluorination reaction (continuous or semi-batch mode) using HF with simultaneous removal of by-product HCl and the product 1233xf, (2) recycle of unreacted 240db and HF together with under-fluorinated by-products back to (1), (3) separation and purification of by-product HCl, (4) separation of excess HF back to (1), and (5) purification of final product, 1233xf.

Figure 1:
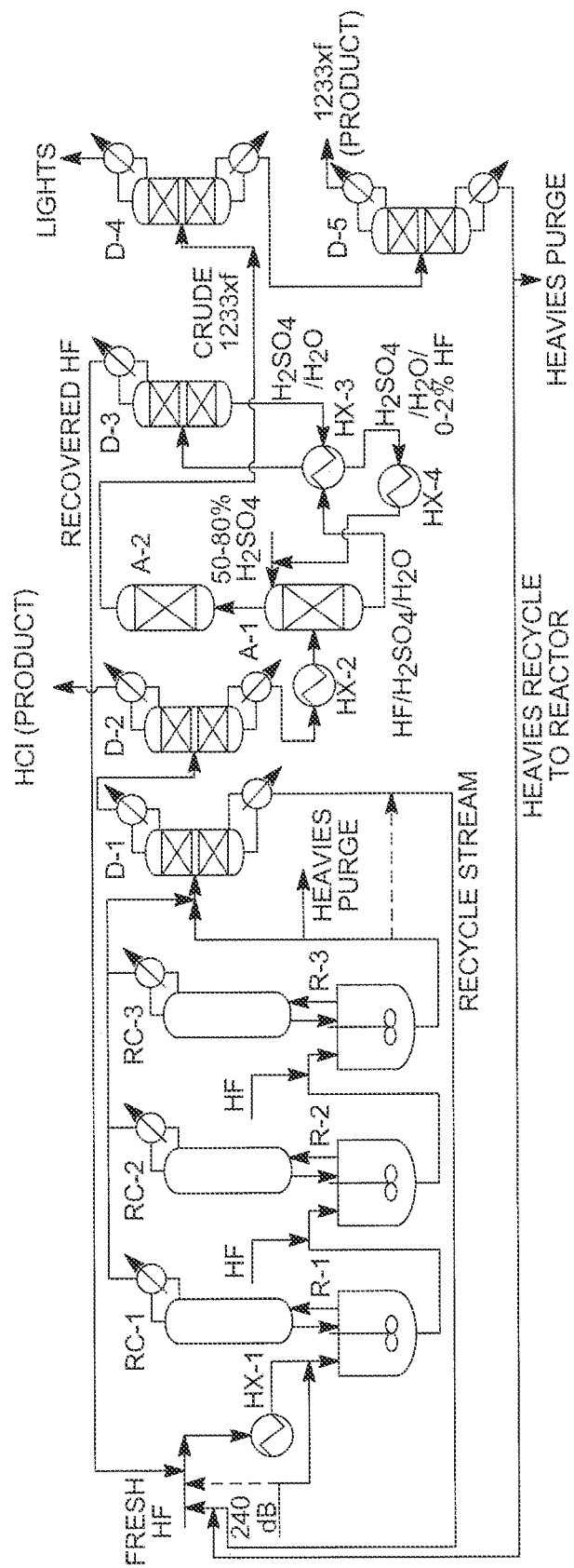
FIG. 1 shows a schematic depiction of an integrated liquid phase synthesis of 1233xf according to a preferred embodiment of the invention.
Figure 2:
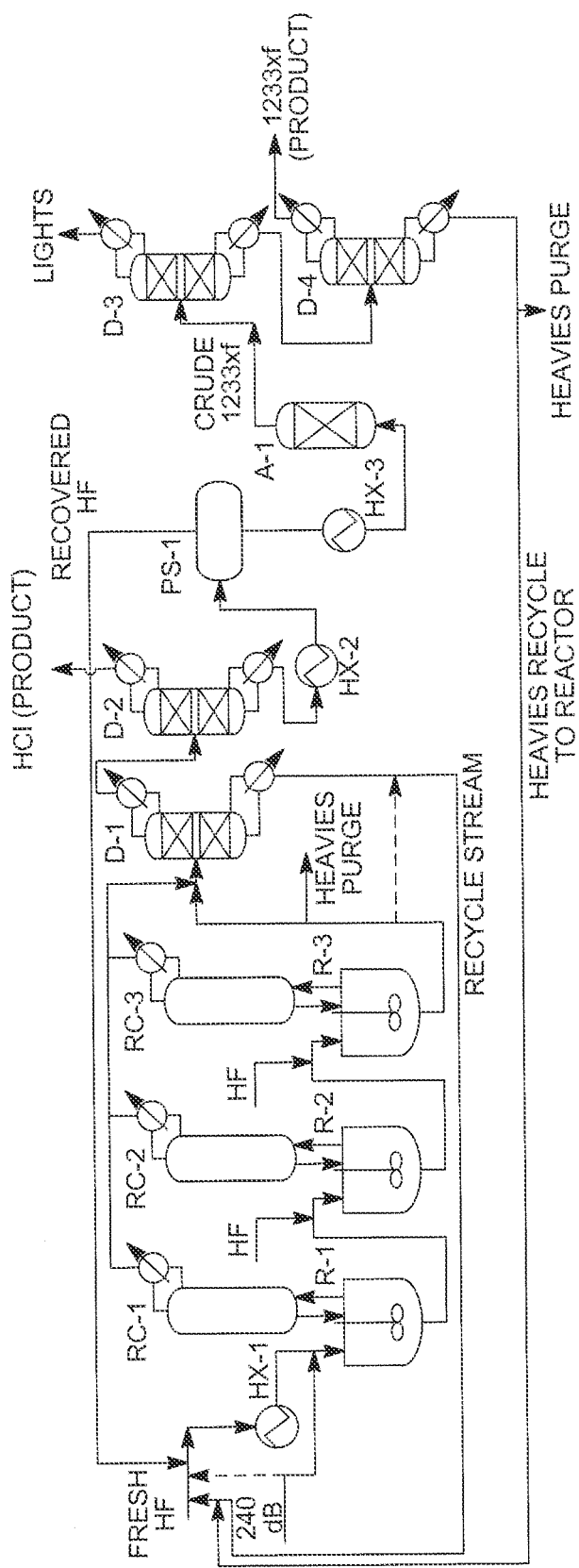
FIG. 2 shows a schematic depiction of an integrated liquid phase synthesis of 1233xf according to another preferred embodiment of the invention.

The relative positions of these operations in certain preferred embodiments are shown in FIGS. 1 and 2.

(1) Reactor and Stripping Column

Preferably the reactor is constructed from materials which are resistant to the corrosive effects of the HF and HCl, such as Hastelloy-C, Inconel, Monel, Incoloy, or fluoropolymer-lined steel vessels. The reactor is equipped with an agitator. Such liquid-phase fluorination reactors are well known in the art. The reactor is equipped with a stripping column which permits the desired product to leave, along with by-product HCl, traces of light organics (principally 245cb and 244bb), and sufficient anhydrous hydrogen fluoride (AHF) to form the azeotropes, while retaining the bulk of the HF, plus under-fluorinated organics.

In preferred embodiments more than one fluorination reactors are connected in a series to increase throughput. In a preferred embodiment, the reaction is conducted in a train of agitated, temperature-controlled reactors connected in a series and containing liquid reactants. One or more feeds comprising hydrogen fluoride and 1,1,1,2,3-pentachloropropane enters the first reactor where they contact each other in a liquid phase.

The resulting reaction produces a gas phase product comprising 1233xf as well as various other by-products including HCl, some under-fluorinated intermediates, and a small amount of over-fluorinated by-products. The gas phase product leaves the liquid phase reactor and enters an integrated stripping column (operating in reflux mode) which permits the desired product to leave (along with by-product HCl, over-fluorinated by-products and traces under-fluorinated intermediates, and sufficient anhydrous hydrogen fluoride (AHF) to at least form the azeotropes), while retaining the bulk of the HF, plus under-fluorinated organics.

The products exiting the top of the stripping column are fed into recycle column (2). The stream of under-fluorinated reaction products and unreacted 240db and HF is taken from the bottom of the first fluorination reactor and fed together with required amount of fresh HF to the second fluorination reactor that is operated similar to first fluorination reactor. In some embodiments more than two reactors are connected in the series. The stream from the bottom of the last fluorination reactor is fed to the recycle column (2).

HF and 240db can be charged to the fluorination reactor and the reaction can be initiated immediately upon heating to the desired reaction temperature. The flow of HF to the first fluorination reactor can be established, and addition of the 1,1,1,2,3-pentachloropropane can be started immediately to cause continuous reaction.

Alternatively, a large amount of the same 1,1,1,2,3-pentachloropropane can be added at one time as a batch charge, and then HF can be added gradually to the reactor (a semi-batch operation). Alternatively, a large amount of HF can be added at one time as a batch charge, and then the same 1,1,1,2,3-pentachloropropane can be added gradually to the reactor (a semi-batch operation).

In some embodiments utilizing multiple fluorination reactors connected in a series, the HF can be fed to all of the reactors to maintain proper ratio of HF to organics. Proper temperature control of the coolant and sufficient reflux action are desirable for optimum operation of the stripping column to be effective.

General operating conditions which have been found to work well for the reaction and stripping column are: Operating pressure of 100 psig to 500 psig maintained by a control valve on the exiting flow from the stripping column; reactor temperature of 65° C. to 175° C., primarily supplied by steam flow into the reactor jacket; application of −40° C. to −25° C. brine cooling to the heat exchanger on top of the stripping column to induce reflux; temperature in the center portion of the stripper from about 5° C. to 60° C. below that in the reactor; additional heat input by superheating the HF feed with high-pressure steam to 70° C. to 180° C.

It has been discovered that maintaining the reaction under the operating conditions, particularly, a temperature range of 65° C. to 175° C., more preferably 85° C. to 155° C., and most preferably 95° C. to 150° C., which produces 1233xf in high yield.

(2) Recycle Column

The stream exiting the top of stripping columns attached to the fluorination reactors comprising mainly 1233xf, HF, and HCl (with some minor components including partially fluorinated intermediates and by-products, over-fluorinated by-products), then enters a recycle column. The stream of unreacted HF and 240db, under-fluorinated by-products from the bottom of last fluorination reactor is also fed to the recycle column.

A stream comprising mainly unreacted 1,1,1,2,3-pentachloropropane, partially fluorinated intermediates, and the majority of the HF exits the bottom of the recycle column and is recycled back to the first liquid phase reactor. Optionally it can be fed to any of the reactor in the series. A stream comprising mainly 1233xf, HF, and HCl exits the top of the recycle column and enters HCl recovery column.

(3) Removal of HCl

The HCl formed continuously during the reaction is removed from the reactor due to its volatile nature, and flows through the attached distillation column without condensing. The material can then be purified and collected for sale (or further purification) by using a low-temperature HCl distillation column. High purity HCl is isolated and can be absorbed in de-ionized water as concentrated HCl for sale.

(4) Separation and Recycle of Excess HF Back to (1)

The bottoms stream from the HCl removal column (3) that contains crude product mixture of 1233xf and HF (in some embodiments about 30 wt % 1233xf) is fed to a sulfuric extractor or a phase separator for removal of HF from this mixture. HF is either dissolved in the sulfuric acid or phase separated from the organic mixture. For embodiments utilizing a sulfuric acid adsorption system, the HF is then desorbed from the sulfuric acid/HF mixture by stripping distillation and recycled back to the reactor. For embodiments utilizing a phase separator, HF is phase-separated and recycled back to the reactor. The organic mixture either from the overhead of the sulfuric acid extractor or from the bottom layer of the phase separator may require treatment (scrubbing or adsorption) to remove traces of HF before it is fed to the next unit operation (5).

(5) Purification of Final Product—1233xf

Purification of final product preferably comprises two continuously operating distillation columns. The first ($1^{st}$) column is used to remove light ends from the 1233xf and the second ($2^{nd}$) column is used to remove the heavier components, primarily the under-fluorinated intermediates, which are recycled to fluorination reactor (1) or collected for further use or disposal. In certain embodiments, it is desirable to have a purge of heavy by-products from this stream.

Referring to FIG. 1, shown is the synthesis of 1233xf via a liquid phase reaction integrated process utilizing three reactors connected in series (R-1, R-2, and R-3), having sulfuric acid HF recovery, and recycle column after the reactors. Here, liquid phase reactor R-1 is first charged with an required amounts of anhydrous hydrogen fluoride and 1,1,1,2,3-pentachloropropane. Preferably the reactor is constructed from materials which are resistant to the corrosive effects of the HF and HCl, such as Hastelloy-C, Inconel, Monel, Incoloy, or fluoropolymer-lined steel vessels. Such liquid-phase fluorination reactors are well known in the art. After reactor is charged with HF and 240db an agitator is turned on to achieve a good agitation.

The reaction mixture is then heated to about 85° C. to 150° C. where the fluorination reaction between 1,1,1,2,3-pentachloropropane and HF is initiated. Continuous 1,1,1,2,3-pentachloropropane and HF (in a stoichiometric excess) feeds are simultaneously fed to heater HX-1 and then into a liquid phase reactor R-1. Optionally, 1,1,1,2,3-pentachloropropane is fed directly into reactor R-1 and not through heater HX-1.

The operating pressure of R-1 is in the range of 75 psig to 500 psig (preferably 185 psig to 400 psig) is maintained by a control valve on the exiting flow from the stripping column RC-1 and the reactor temperature is kept in the range of 65° C. to 175° C. (preferably 100° C. to 140° C.) primarily supplied by steam flow into the reactor jacket. A stripping column RC-1 is connected to the reactor, R-1, and serves the purpose of knocking down and returning some HF, partially fluorinated intermediates, and some unreacted 1,1,1,2,3-pentachloropropane back to the reactor for further reaction.

The stream exiting the top of stripping RC-1 comprising mainly 1233xf, HF, and HCl (with some minor components including partially fluorinated intermediates and by-products, and over-fluorinated by-products), then enters then enters recycle column D-1.

When the desired level in the first fluorination reactor is achieved a stream of unreacted HF, unreacted 1,1,1,2,3-pentachloropropane, and under-fluorinated intermediates is fed to second fluorination reactor R-2. The feed of fresh HF is also fed to R-2 to maintain proper HF to organics ratio. Reactor R-2 is equipped with stripping column RC-2 that is operated similar to RC-1. Reactor R-2 is maintained at a temperature of from 115° C. to 150° C. and a pressure of from about 170 psig to 425 psig.

The stream exiting the top of stripping RC-2 comprising mainly HCFO-1233xf, HF, and HCl (with some minor components including partially fluorinated intermediates and by-products, and over-fluorinated by-products), then enters then enters recycle column D-1.

When the desired level in the second fluorination reactor is achieved a stream of unreacted HF, unreacted 1,1,1,2,3-pentachloropropane, and under-fluorinated intermediates is fed to third fluorination reactor R-3. The feed of fresh HF is also fed to R-3 to maintain proper HF to organics ratio. Reactor R-3 is equipped with stripping column RC-3 that is operated similar to RC-1 and RC-2. Reactor R-3 is maintained at a temperature range of 125° C. to 160° C. and pressure range of about 160 psig to 450 psig.

The stream exiting the top of stripping RC-3 comprising mainly 1233xf, HF, and HCl (with some minor components including partially fluorinated intermediates and by-products, and over-fluorinated by-products), then enters recycle column D-1.

When the desired level in the third fluorination reactor is achieved a stream of unreacted HF, unreacted 1,1,1,2,3-pentachloropropane, and under-fluorinated intermediates is fed to the recycle column D-1. Optionally, heavy by-products are removed from this stream by establishing a small heavies purge continuous or intermittent side stream.

The recycle column D-1 is operated in a such a way that a stream comprising mainly unreacted 1,1,1,2,3-pentachloropropane, partially fluorinated intermediates, and the majority of the HF exits the bottom of the recycle column and is recycled back to the liquid phase reactor R-1 via vaporizer HX-1. A stream comprising mainly 1233xf, HF, and HCl exits the top of the recycle column and enters HCl column D-2. A stream comprising mainly HCl by-product exits the top of the HCl column and is fed to an HCl recovery system. The recovered HCl by-product can be sold for profit.

The HCl column bottoms stream consisting mainly of 1233xf and HF are then fed into an HF recovery system. The HF recovery system starts with the crude 1233xf/HF stream being vaporized in heat exchanger HX-2 and fed into HF absorption column A-1. Here a liquid stream of 50% to 80% $H_2SO_4$ contacts the gaseous 1233xf/HF stream and absorbs the majority of the HF. The stream exiting the bottom of A-1 comprises $HF/H_2SO_4/H_2O$ and is fed to heat exchanger HX-3 where it is heated to a temperature sufficient to flash the majority of the HF along with small amounts of $H_2O$ and $H_2SO_4$. This stream is fed to HF recovery distillation column D-2. The liquid remaining after the HF is flashed off in HX-3 consisting mainly of $H_2SO_4$ and $H_2O$ (with 0 to 2% HF) is cooled in HX-4 and recycled back to HF absorption column A-1.

The HF recovery column, D-3, bottoms stream comprising mainly $H_2SO_4$ and $H_2O$ are recycled back to heat exchanger HX-3 Anhydrous HF is recovered from the top of the HF recovery column, D-3, and is recycled back to the reactor R-1 via vaporizer HX-1. The stream exiting the top of HF absorption column A-1 comprising mainly 1233xf (trace HF) is sent forward to a polishing system A-2 where the gaseous stream contacts a water or a caustic solution to remove trace HF and is subsequently dried with a desiccant.

Acid free crude product exiting absorber A-2 is sent to the first of two purification columns, D-4. A stream exiting the top of the column D-4 consists mainly of reaction by-products that have boiling points lower than that of 1233xf. The stream exiting the bottom of lights column D-4 consisting mainly of 1233xf and heavier by-products is fed to product recovery distillation column D-5. Product grade 1233xf exits the top of the column to product storage. The product column bottoms consist mainly of reaction by-products with boiling points higher than that of 1233xf is then fed to vaporizer HX-1 and then fluorination reactor R-1.

Referring to FIG. 2, shown is the synthesis of 1233xf via a liquid phase reaction integrated process utilizing three reactors connected in series (R-1, R-2, and R-3), a phase separation HF recovery system, and recycle column after the reactor. Here, liquid phase reactor R-1 is first charged with an required amounts of anhydrous hydrogen fluoride and 1,1,1,2,3-pentachloropropane. Preferably the reactor is constructed from materials which are resistant to the corrosive effects of the HF and HCl, such as Hastelloy-C, Inconel, Monel, Incoloy, or fluoropolymer-lined steel vessels. Such liquid-phase fluorination reactors are well known in the art. After reactor is charged with HF and 240db an agitator is turned on to achieve a good agitation.

The reaction mixture is then heated to about 85° C. to 150° C. where the fluorination reaction between 1,1,1,2,3-pentachloropropane and HF is initiated. Continuous 1,1,1,2,3-pentachloropropane and HF (in a stoichiometric excess) feeds are simultaneously fed to heater HX-1 and then into a liquid phase reactor R-1.

Optionally, 1,1,1,2,3-pentachloropropane is fed directly into reactor R-1 and not through heater HX-1. The operating pressure of R-1 is in the range of 75 psig to 500 psig (preferably 185 psig to 450 psig) is maintained by a control valve on the exiting flow from the stripping column RC-1 and the reactor temperature is kept in the range of 65° C. to 175° C. (preferably 100° C. to 140° C.) primarily supplied by steam flow into the reactor jacket. A stripping column RC-1 is connected to the reactor, R-1, and serves the purpose of knocking down and returning some HF, partially fluorinated intermediates, and some unreacted 1,1,1,2,3-pentachloropropane back to the reactor for further reaction.

The stream exiting the top of stripping RC-1 comprising mainly 1233xf, HF, and HCl (with some minor components including partially fluorinated intermediates and by-products, and over-fluorinated by-products), then enters then enters recycle column D-1.

When the desired level in the first fluorination reactor is achieved a stream of unreacted HF, unreacted 1,1,1,2,3-pentachloropropane, and under-fluorinated intermediates is fed to second fluorination reactor R-2. The feed of fresh HF is also fed to R-2 to maintain proper HF to organics ratio. Reactor R-2 is equipped with stripping column RC-2 that is operated similar to RC-1. Reactor R-2 is maintained at a temperature range of 115° C. to 150° C. and pressure range of about 170 psig to 425 psig.

The stream exiting the top of stripping RC-2 comprising mainly 1233xf, HF, and HCl (with some minor components including partially fluorinated intermediates and by-products, and over-fluorinated by-products), then enters then enters recycle column D-1.

When the desired level in the second fluorination reactor is achieved a stream of unreacted HF, unreacted 1,1,1,2,3-pentachloropropane, and under-fluorinated intermediates is fed to third fluorination reactor R-3. The feed of fresh HF is also fed to R-3 to maintain proper HF to organics ratio. Reactor R-3 is equipped with stripping column RC-3 that is operated similar to RC-1 and RC-2. Reactor R-3 is maintained at a temperature range of from 125° C. to 160° C. and pressure range of from about 160 psig to 450 psig.

The stream exiting the top of stripping RC-3 comprising mainly 1233xf, HF, and HCl (with some minor components including partially fluorinated intermediates and by-products, and over-fluorinated by-products), then enters then enters recycle column D-1.

When the desired level in the third fluorination reactor is achieved a stream of unreacted HF, unreacted 1,1,1,2,3-pentachloropropane, and under-fluorinated intermediates is fed to the recycle column D-1. Optionally, heavy by-products are removed from this stream by establishing a small heavies purge continuous or intermittent side stream.

The recycle column D-1 is operated in a such a way that a stream comprising mainly unreacted 1,1,1,2,3-pentachloropropane, partially fluorinated intermediates, and the majority of the HF exits the bottom of the recycle column and is recycled back to the liquid phase reactor R-1 via vaporizer HX-1. A stream comprising mainly 1233xf, HF, and HCl exits the top of the recycle column and enters HCl column D-2. A stream comprising mainly HCl by-product exits the top of the HCl column and is fed to an HCl recovery system. The recovered HCl by-product can be sold for profit. The HCl column bottoms stream consisting mainly of 1233xf and HF are then fed into an HF recovery system.

The HF recovery system starts with the 1233xf/HF stream being fed into heat exchanger HX-2 where it is pre-cooled to temperatures below 0° C. and then enters phase separation vessel PS-1. Here the stream temperature is maintained or further cooled to −40° C. to 0° C. The HF rich top layer (less than 10% 1233xf) is recycled back to the liquid phase reactor R-1. The organic rich bottom layer containing mainly 1233xf (less than 4% HF) is sent to vaporizer HX-3 and then forward to a polishing system A-1 where the gaseous stream contacts water or a caustic solution to remove trace HF and is subsequently dried with a desiccant. Acid free crude product exiting absorber A-1 is sent to the first of two purification columns, D-3.

A stream exiting the top of the column D-3 consists mainly of reaction by-products that have boiling points lower than that of 1233xf. The stream exiting the bottom of lights column D-3 consisting mainly of 1233xf and heavier by-products is fed to product recovery distillation column D-4. Product grade 1233xf exits the top of the column to product storage. The product column bottoms consist mainly of reaction by-products with boiling points higher than that of 1233xf is then fed to vaporizer HX-1 and then to fluorination reactor R-1.

Optionally, the stream exiting the bottom of the product recovery distillation column, D-4 can be recycled back to first liquid phase reactor R-1. In any of these options a heavies purge stream from the bottom of the product recovery distillation column, D-4, will be required to prevent build-up of high boiling impurities in the purification system. The heavies purge stream is collected for later use or waste disposal.

EXAMPLES

Example 1

As part of the development of a liquid phase process for making 1233xf an experiment is run using no catalyst. The experiment is run in a 1-gallon Parr reactor in a batch mode. For the experiment 282.9 grams of HF and 246.2 grams of 240db (1,1,1,2,3-pentachloropropane) (12.4 to 1 mole ratio HF:240db) are charged to the reactor at room temperature. The mixer is then turned on ensuring the reactor contents were well mixed. Then the reactor is heated to the desired temperature. Upon heating the pressure begins to rise as HCl by product is produced as a result of a fluorination reaction.

The reactor is heated to about 110° C. over several hours and then the temperature is held constant. The pressure is controlled in the range of 250 psig to 325 psig by venting off the HCl generated in the reaction to a dry-ice chilled dry ice trap (DIT). At the completion of the reaction after about 9.5 hours, which is determined by lack of HCl generation, the pressure from the reactor is vented into the DIT. The crude product from DIT is transferred into a 1 L Monel absorption cylinder (frozen in dry-ice) with about 400 grams of water. The absorption cylinder is allowed to warm up to room temperature and a sample of an organic layer that has formed in the cylinder (aqueous and organic layers are present in the cylinder upon discharge) is taken and analyzed by GC.

GC results show 0.42 GC % 245cb, 97.23 GC % 1233xf, 1.39 GC % 244bb, balance under-fluorinated intermediates (241db and 242db). The amount of organic collected is later quantified by further analysis of the different phases and amounted to 75.0 grams.

The organic remaining in the reactor after venting is recovered by quenching the reactor with about 300 grams to 400 grams of water to absorb HF and HCl, and then adding about 100 grams of carbon tetrachloride. The reactor is then opened and its contents discharged into a plastic bottle. The organic is separated from the aqueous phase by use of a separatory funnel. The amount of heavies collected from the reactor is calculated by subtracting the weight of $CCl_4$ added to the reactor from the total weight of organic phase collected and amounts to 96.9 grams.

GC/MS and GC analysis of the organic layer reveals 3 distinct peaks attributed to under-fluorinated species 241db, 91.057 GC %, 242dc, 0.760 GC %, and the starting material 240db, 8.183 GC %. The overall conversion of 240db was calculated to be 97%.

Example 2

The experiment described in Example 1 is repeated using the same equipment and procedure. The reactor is heated to 110° C. and held. However, the experiment is not allowed to go to completion. After about 6.5 hours the reactor pressure reaches 320 psig and the experiment is stopped. 382.7 grams of HF and 244.1 grams of 240db are initially charged to the reactor. As shown below in Table I, the results are similar to those of Example 1, but with a lower conversion of 240db.

TABLE I

| Charged to reactor | Weight (moles) |
|---|---|
| HF | 392.7 grams (16.485 moles) |
| 240db | 244.1 grams (1.129 moles) |
| Collected reaction products | Weight |
| Volatile products form DIT | 76.1 grams (0.2 GC % 245cb, 97.5 GC % 1233xf, 2.1 GC % 244bb (balance 241db and 242dc) |
| Heavies from reactor | 121.4 grams (1.713 GC % 242db, 58.691 GC % 241db, 39.596 GC % 240db) |

Comparative Example 1

This comparative example shows that 240db is more stable than its unsaturated derivatives such as tetrachloropropenes in the presence of hydrogen fluoride at elevated temperatures.

As part of the development of a liquid phase process for making 1233xf an experiment was run using 1,1,2,3-tetrachloropropene as a starting material. The experiment used the same a 1-gallon Parr reactor as described in Examples 1 and 2 and was run in a batch. The empty reactor was first charged with 327 grams of 1,1,2,3-tetracholopropene. Then 557.5 grams of HF were charged into the reactor at room temperature. The mixer was then turned on ensuring the reactor contents were well mixed. Then the reactor was heated to 149° C.

Upon heating the pressure began to rise as HCl by product was produced as a result of a fluorination reaction. The pressure was controlled in the range of 490 psig to 497 psig by venting off the HCl generated in the reaction to a dry-ice chilled DIT. The reactor was held at 149° C. for about 4 hours. The volatile reaction products collected in the DIT and the reactor residue were worked up and analyzed the same way as described in Example 1. Analysis of the reaction products revealed that the selectivity to 1233xf was about 20%. Remaining 80% of 1,1,2,3-tetrachloropropene starting material were converted to unknown tar-like compounds. This comparative example shows the benefits of starting with saturated chloroalkane, HCC-240db, as no tar-like by-products were observed in Example 1 when the reaction was run at similar conditions.

Comparative Example 2

This comparative example shows that the use of a fluorination catalyst for the fluorination reaction of 240db to 1233xf results in the formation of a large amount of oligomers, dimers, and tars.

As part of the development of a liquid phase process for making 1233xf an experiment was run using a liquid phase fluorination catalyst. The experiment used a 1 liter agitated autoclave and was run in a batch mode and was called Exp #4. The empty reactor was first charged with 84.3 grams of SbCl$_5$ liquid fluorination catalyst. Then 402.6 grams of HF was charged into the reactor at room temperature which was immediately followed by a pressure rise in the reactor due to the generation of HCl as the catalyst became fluorinated.

After venting the pressure (HCl) resulting from the reaction of HF with the catalyst, 152.3 grams of HCC-240db was charged to reactor. The mixer was then turned on ensuring the reactor contents were well mixed. Then the reactor was heated to 90° C. Upon heating the pressure began to rise as HCl by product was produced as a result of a fluorination reaction. The pressure was controlled in the range of 325 psig to 330 psig by venting off the HCl generated in the reaction to a dry-ice chilled trap. The reactor was held at 90° C. for about 1 hour.

The volatile reaction products collected in the DIT and the reactor residue were worked up and analyzed the same way as described in Example 1. The volatile reaction products were the same as those from the experiments run without catalyst described in Examples 1 and 2, but the organic remaining in the reactor after venting were different. This time the organic layer (CCl$_4$ with dissolved organic) was a dark brown/black color and was much more viscous than the organic layer collected in the non catalytic experiments and GC analysis indicated the presence of multiple oligomeric by-products and tars. No HCC-240db or under-fluorinated species, HCFC-241db and HCFC-242db, were present.

Experimental conditions and results of GC analysis of the reaction products are presented in the Table II below.

TABLE II

| Collected reaction products | |
| --- | --- |
| | Weight (moles) |
| SbCl$_5$ | 84.3 grams (0.282 moles) |
| HF | 302.6 grams (15.13 moles) |
| 240db | 152.3 grams (0.704 moles) |

TABLE II-continued

| Collected reaction products | |
| --- | --- |
| | Weight |
| Volatile products form DIT | 62.3 grams (11.06 GC % 245cb, 11.0 GC % 1233xf, 16.2 GC % 244fa, 13.7 GC % 1223xd, 10.4 C$_6$H$_3$Cl$_2$F$_7$ GC area %, 37% unknowns) |
| Heavies from reactor | 43.7 grams (multiple oligomers and tars) |

Example 3

A series of three (3) continuously stirred reactors with attached stripping columns is used to produce crude 1233xf product. There is a bottom drain on the first reactor that feeds the second reactor and a drain on the second reactor that feeds the third reactor. The overhead stream that exits each of the three stripping columns are connected to combine all 1233xf crude and HCl produced and fed forward for separation into individual components.

To the lead (first) reactor is continuously fed a 15:1 mole ratio of HF:240db. The reactor temperature is maintained at about 140° C. The reactor pressure is controlled at about 400 psig. HF, HCl, and crude 1233xf exit the top of the attached stripping column continuously. The reactor is drained continuously to the second reactor at a rate that maintains a near constant level in the reactor. The lead reactor achieves a 70% conversion of 240db and a yield of 50% of 1233xf crude. The organic composition of the material being drained to the second reactor is about 40% 240db, 55% 241db, and 5% 242db. HF is also present in this stream. Fresh HF is added to the second reactor to make up for rectifier column overhead losses.

The second reactor is run at a 375 psig and is maintained at 135° C. HF, HCl, and crude 1233xf exit the top of the attached stripping column continuously. The reactor is drained continuously to the third reactor at a rate that maintains a near constant level in the reactor. The second reactor achieves a 90% conversion of 240db and a yield of 70% of 1233xf crude. The organic composition of the material being drained to the second reactor is about 33% 240db, 62% 241db, and 5% 242db. HF is also present in this stream. Fresh HF is added to the third reactor to make up for rectifier column overhead losses.

The third reactor is run at a 350 psig and is maintained at 130° C. HF, HCl, and crude 1233xf exit the top of the attached stripping column continuously. The reactor is drained continuously to a recycle column at a rate that maintains a near constant level in the reactor. The third reactor achieves a 100% conversion of 240db and a yield of 95% of 1233xf crude. The organic composition of the material being drained to the recycle column is about 95% 241db, and 5% 242db. HF is also present in this stream.

Example 4

This example demonstrates the recycle column operation which recovers excess HF, unreacted 240db, and under-fluorinated intermediates for recycle back to the reactor.

The reactor effluent stream from a fluorination reactor producing 1233xf was continuously fed directly to a recycle distillation column. The stream contained HF, HCl, and 1233xf crude product. The crude product contained some over-fluorinated intermediates, under-fluorinated intermediates, and unreacted organic feed stock. The distillation column consisted of a 10 gallon reboiler, 2 inch ID by 10 foot column packed with propack distillation packing and a shell and tube condenser. The column had about 30 theoretical plates. The distillation column was equipped with reboiler level indicator, temperature, pressure, and differential pressure transmitters.

The distillation column was run continuously at pressure of about 60 psig and differential pressure of about 15 inches of $H_2O$. The stream exiting overhead from the top of the column consisted of HCl, over-fluorinated intermediates, 1233xf, and some of the HF. A GC analysis of the organic portion of the stream showed the purity of 1233xf was greater than 99 GC area %.

The stream exiting the bottom of the reboiler consisted of HF, under-fluorinated intermediates, and unreacted organic feed stock and were recycled back to the fluorination reactor.

Example 5

This example illustrates the recovery of anhydrous HF from a mixture of HF and 1233xf according to certain preferred embodiments of the present invention.

A mixture consisting of about 75 wt. % 1233xf and about 25 wt. % HF is vaporized and fed to the bottom of a packed column at a feed rate of about 2.9 lbs per hour for about 4 hours. A stream of about 80 wt. % sulfuric acid (80/20 $H_2SO_4$/ $H_2O$) with about 2% HF dissolved therein is fed continuously to the top of the same packed column at a feed rate of about 5.6 lbs per hour during the same time frame. A gaseous stream exiting the top of the column comprises 1233xf with less than 1.0 wt. % HF therein. The concentration of HF in the sulfuric acid in the column bottoms increases from 2.0 wt. % to about 15 wt. %.

The column bottoms containing sulfuric acid and about 15 wt. % HF are collected and charged into a 2 gallon teflon vessel. The mixture is heated to about 140° C. to vaporize and flash off the HF product, which is collected. The collected HF product contains about 6000 ppm water and 500 ppm sulfur.

The HF collected from flash distillation is distilled in a distillation column and anhydrous HF is recovered. The recovered anhydrous HF contains less than 50 ppm of sulfur impurities and less than 100 ppm water.

Example 6

This example illustrates the phase separation of a mixture of 1233xf and HF which form a heterogeneous mixture.

60.77 grams of crude 1233xf and 34.91 grams of HF were mixed together in a Teflon cell and 2 liquid phases were visually observed. The mixture was allowed to sit until it reached ambient temperature of about 24° C. The upper and lower phases were sampled and analyzed by Ion Chromatography to determine HF concentration. The lower organic rich layer had 2.2 wt % HF and the upper HF rich layer had 62.96 wt % HF.

Example 7

This example demonstrates the purification of the acid free 1233xf crude product.

120 lbs of 1233xf crude product collected after HCl and HF removal was charged to a batch distillation column. The crude material contained about 96 GC area % 1233xf and 4 GC area % impurities. The distillation column consisted of a 10 gallon reboiler, 2 inch ID by 10 foot column packed with propack distillation packing and a shell and tube condenser. The column had about 30 theoretical plates. The distillation column was equipped with reboiler level indicator; temperature, pressure, and differential pressure transmitters. The batch distillation was run at pressure of about 90 psig and differential pressure of about 17 inches of $H_2O$. About 7 lbs of a lights cut was recovered which consisted of mainly 245cb, trifluoropropyne, 244bb, and 1233xf. 110 lbs of 99.9+ GC area % 1233xf were collected. The reboiler residue amounting to about 3 lbs was mainly 244bb, 1233xf, 1232xf, and a C6 compound (dimer). The recovery of 99.8+ GC area % pure 1233zd(E) was 94.8%.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. An integrated system for producing 1233xf comprising:
   (a) one or more feed streams cumulatively comprising hydrogen fluoride and 1,1,1,2,3-pentachloropropane;
   (b) a liquid phase reactor system consisting of a series of two or more reactors each fed by its predecessor, each combined with attached stripping column supplied with low-temperature cooling, maintained at a first temperature of about 65° C. to about 175° C., wherein said liquid phase reactor series is fluidly connected to said one or more feed streams;
   (c) a stripping system comprising a stripping column, a reflux stream fluidly connected to said stripping column, and a combined first crude product stream fluidly connected to said stripping column, wherein said reflux stream is fluidly connected to said lead liquid phase reactor;
   (d) a hydrogen chloride removal system comprising a first distillation column, a hydrogen chloride by-product stream fluidly connected to said first distillation column, and a second crude product stream fluidly connected to said first distillation column, wherein said first distillation column is fluidly connected to said stripping column;
   (e) a hydrogen fluoride recovery system comprising a sulfuric acid absorption and recycle system or a phase separation vessel, a second recycle stream comprising hydrogen fluoride fluidly connected to said sulfuric acid absorption and recycle system or a phase separation vessel, a third product stream comprising 2-chloro-3,3,3-trifluoropropene fluidly connected to said sulfuric acid absorption and recycle system or a phase separation vessel, wherein said sulfuric acid absorption and recycle system or a phase separation vessel is fluidly connected to said second crude product stream; and (f) a 2-chloro-3,3,3-trifluoropropene purification system comprising a second distillation column fluidly connected to said third product stream; a final product stream comprising 2-chloro-3,3,3-trifluoropropene fluidly connected to said second distillation column; a second by-product stream fluidly connected to said distillation column.

2. The system of claim 1, wherein the reaction temperature range is from 85° C. to 155° C.

3. The system of claim 1, wherein the reaction temperature range is from 95° C. to 150° C.

* * * * *